United States Patent
Hirata et al.

[11] Patent Number: 5,549,664
[45] Date of Patent: Aug. 27, 1996

[54] ARTIFICIAL BLOOD VESSEL

[75] Inventors: Yoshimi Hirata; Noriaki Kaneko; Masahiro Moriwaki; Kanetake Oura, all of Ichihara, Japan

[73] Assignee: UBE Industries, Ltd., Ube, Japan

[21] Appl. No.: 236,694

[22] Filed: May 2, 1994

Related U.S. Application Data

[63] Continuation of Ser. No. 856,150, filed as PCT/JP91, 01027, published as WO92/02195, Feb. 29, 1992, abandoned.

[30] Foreign Application Priority Data

Jul. 31, 1990 [JP] Japan ..................................... 2-201147
Feb. 8, 1991 [JP] Japan ..................................... 3-037810

[51] Int. Cl.$^6$ .................................................... A61F 2/06
[52] U.S. Cl. ................... 623/1; 600/36; 623/12
[58] Field of Search .................... 623/1, 11, 12; 600/36; 606/194, 195, 151–158; 604/8

[56] References Cited

U.S. PATENT DOCUMENTS

| | | | |
|---|---|---|---|
| 4,093,677 | 6/1978 | Ferruti et al. | 623/2 |
| 4,164,045 | 8/1979 | Bokros et al. | 623/1 |
| 4,459,252 | 7/1984 | MacGregor | 623/1 |
| 4,604,762 | 8/1986 | Robinson . | |
| 4,743,252 | 5/1988 | Martin, Jr. et al. | 623/1 |
| 4,813,966 | 3/1989 | Gilding et al. | 623/1 |
| 4,850,999 | 7/1989 | Planck | 623/1 |
| 4,857,069 | 8/1989 | Kira . | |
| 4,878,907 | 11/1989 | Okada et al. | 623/1 |
| 4,954,127 | 9/1990 | Kira . | |
| 4,986,832 | 1/1991 | Kaneko et al. | 623/1 |
| 4,997,440 | 3/1991 | Dumican | 623/11 |
| 5,053,048 | 10/1991 | Pinchuk | 623/1 |

FOREIGN PATENT DOCUMENTS

| | | |
|---|---|---|
| 0271216 | 6/1988 | European Pat. Off. . |
| 0308102 | 3/1989 | European Pat. Off. ................... 623/1 |
| 0332371 | 9/1989 | European Pat. Off. . |
| 57-150954 | 9/1982 | Japan . |
| 60-182959 | 9/1985 | Japan . |
| 61-185271 | 8/1986 | Japan . |
| 61-238238 | 10/1986 | Japan . |
| 61-263448 | 11/1986 | Japan . |
| 62-258666 | 11/1987 | Japan . |
| 1-64650 | 3/1989 | Japan . |
| 1-198544 | 8/1989 | Japan . |
| 2077107 | 12/1981 | United Kingdom ....................... 623/1 |

*Primary Examiner*—Debra S. Brittingham
*Attorney, Agent, or Firm*—Frishauf, Holtz, Goodman, Langer & Chick, P.C.

[57] ABSTRACT

An artificial blood vessel which has excellent long-term patency and can be used stably in a living body for a long time. The artificial blood vessel has improved durability under pulsation and can withstand puncturing. The artificial blood vessel is made of an elastomer containing a multiplicity of cells throughout the structure thereof and comprises a layer (A) containing closed cells having no communicability therebetween; and a layer (B) containing open cells having mutual communicability therebetween. The surface of the layer (B) which is contiguous to the inner surface of the layer (A) and the wall surfaces of the open cells are coated with a thin film of crosslinked protein of biological origin. The layer (A) may be incorporated with a knitted or woven fabric which is not degradable in a living body. The layer (B) may further contain a synthetic resin short fiber distributed throughout the layer.

29 Claims, 2 Drawing Sheets

ARTIFICIAL BLOOD VESSEL

This application is a Continuation of application Ser. No. 07/856,150, filed Mar. 25, 1992, now abandoned, which is the United States national phase application of International Application No. PCT/JP91/01027 filed Jul. 31, 1991, published as WO92/02195, Feb. 20, 1992.

TECHNICAL FIELD

This invention relates to an artificial blood vessel which has excellent long-term patency and can be used stably in a living body for a long time and to a process for producing the same. More particularly, this invention relates to an artificial blood vessel having improved durability under pulsation and repeated puncturing and to a process for producing the same.

BACKGROUND ART

Implantation of an artificial vessel into a living body first causes primary thrombi to grow on the inner surface thereof which is in contact with blood, and cells propagate themselves thereon to form a neointima, which becomes an antithrombotic intimal tissue. Thus, it is not until the inner wall of the artificial blood vessel is vitalized that the artificial blood vessel can play a role as a substitute for the living blood vessel.

The artificial blood vessel is also required, in view of performance in operations, to have a property of being readily pierced with a suturing needle when anastomosed to a living blood vessel. On the ether hand, puncturing is frequently repeated in blood access for hemodialysis, which is used for connecting arteries and veins. Therefore the vessel wall is required to be durable to repeated puncturing to prevent it from forming a hematoma induced by bleeding after puncturing and to have blood impermeability to prevent formation of seroma due to serum penetrating through the vessel wall. The term "blood impermeability" used herein means that the porosity (amount of leaked water/ $cm^2 \cdot min \cdot 120$ mmHg) is substantially zero.

Japanese Provisional Patent Publication (KOKAI) No. 60-182959/1985 discloses an artificial blood vessel made of an elastomer having a reticular structure containing pores (1 to 100 μm) over the entire thickness, from the inner surface to the outer surface, of the vessel wall. It is described that the reticular structure containing pores which penetrate the vessel wall from the inner surface to the outer surface allows organization of the artificial blood vessel to proceed rapidly and stably when implanted in a living body.

In this type of artificial blood vessel, immobilization of the intimal tissue depends on the so-called anchor effect, i.e. intrusion of the intimal tissue into the pores of the reticular structure. However, such intrusion and growth of the intimal tissue cannot be achieved to a sufficient depth, so that a high anchor effect cannot be expected. Moreover, the pores penetrating through the vessel wall inevitably cause hyperplasia, making immobilization thereof more difficult.

The above patent literature also discloses that the surface of the artificial blood vessel which is brought into contact with blood, i.e. the inner surface of the blood vessel, may be coated with albumin, gelatin, chondroitin sulfate or heparin-containing material for the purpose of improving the antithrombotic property of the artificial blood vessel at the initial stage of implantation to a living body. It is true, however, that the antithrombotic property of the artificial blood vessel at the initial stage of implantation can be improved by this method, but the intimal tissue is prevented from intruding into the pores to show poor adhesion and peels off easily. Thus, the peeled intimal tissue further grows to form pannus which blocks the bloodstream, and in turn causes to form thrombi.

Japanese Provisional Patent Publication (KOKAI) No. 62-25866/1987 discloses an artificial blood vessel made of a porous material, the pores in which a gelatin crosslinked with diisocyanate are filled by impregnation. The gelatin decomposes in a living body to allow new tissue to grow into the porous material. In the artificial blood vessel disclosed in the above patent literature, the optimum decomposition rate of the gelatin is decided depending on the balance between the speed of tissue intrusion or growth and the degree of freedom from blood leakage through the vessel wall having communicability. However, there is a wide individual difference in the growth speed of the neointimal tissue, and it is impossible to decide the balance uniformly. And thus, it is difficult to allow the artificial blood vessel to have a property of vessel wall matched with the individual difference.

Japanese Provisional Patent Publication (KOKAI) No. 61-185271/1986 discloses an artificial blood vessel consisting of an elastomeric porous material forming the structure of the blood vessel and a tubular material made of a fiber which is present in contact with or bonded to some parts of the porous material. However, the pores present in the porous material in this artificial blood vessel communicate with one another from the inner surface to the outer surface, so that the serum penetrates through the vessel wall after implantation to a living body and leaks out of the vessel wall and is thus liable to form a seroma. The pores communicating throughout the vessel wall are liable to be cracked or expanded by the creep induced by pulsation repeated for a long time, leading to the fear of aneurysmic expansion or rupture. Further, the above artificial blood vessel suffers a problem that when it is used for hemodialysis, it is liable to form a hematoma or to be infected by the bleeding through the holes formed by puncturing, so that its durability will notably be reduced by repeating such localized puncturing for a long time.

DISCLOSURE OF INVENTION

The artificial blood vessel according to this invention is made of an elastomer containing a multiplicity of cells throughout the structure thereof and consists of at least two layers:

(A) a layer containing closed cells having no communicability therebetween; and (B) a layer containing open cells having mutual communicability therebetween;

characterized in that the surface of the layer (B) which is present contiguous to the inner surface of the layer (A) and the wall surfaces of said open cells are coated with a thin film of a polymeric material of biological origin (hereinafter referred to as artificial blood vessel A).

The layer (A) may be incorporated with a reinforcing material such as a knitted or woven fabric which is not degradable in a living body (hereinafter referred to as artificial blood vessel B).

The artificial blood vessel B may further be allowed to have a crimped shape.

Incidentally, the layer (B) of the artificial blood vessel A or B may further contain a synthetic resin short fiber distributed therethrough.

The artificial vessels of this invention can be produced as follows:

Artificial Blood Vessel A (a) A solution of an elastomeric material dissolved in a solvent is applied uniformly on the circumference of a mandrel, followed by solidification and desolvation in water to provide a tube.

(b) The elastomer solution is coated at least onto the inner surface of the tube, and a water-soluble powder is deposited on the coated surface. After the thus treated tube is left to stand for a predetermined time, the elastomeric material coated at least onto the inner surface of the tube is solidified and desolvated in water to form a new layer.

(c) The water-soluble powder deposited in the step (b) is removed by dissolving it in a hot water to form open cells having mutual communicability therebetween in the new layer formed in the step (b).

(d) The open cells formed in the step (c) are impregnated with an aqueous solution of a polymeric material of biological origin under reduced pressure and then cooled rapidly, followed by impregnation with a crosslinking agent to form a crosslinked coat of the polymeric material on the surface of the layer and the wall surfaces of open cells formed in the step (c).

Artificial Blood Vessel B

An artificial blood vessel is produced basically in the same manner as in the case of artificial blood vessel A, except that the rod is preliminarily subjected to the following treatment in the step (a):

A tubular knitted or woven fabric which is not degradable in a living body is fitted on the mandrel, and the fabric constituting the tubular structure is impregnated with the solution of an elastomeric material so as to fill the vacancies present therein and to form a uniform layer on the surface of the fabric, followed by solidification and desolvation of the elastomeric material.

Incidentally, prior to the step (b), it is also possible to wind spirally a thread at a constant pitch on the circumference of the tube preliminarily subjected to the above treatment and fitted on a mandrel, and after immersion of the resulting tube in an alcohol, to compress the tube longitudinally under aerobic conditions, followed by reimmersion in the alcohol, removal of the thread, removal of the alcohol by replacement with water, pitch adjustment and drying. It is common in the production of both the blood vessel (A) and blood vessel (B) that the tube may be impregnated first with an aqueous solution of crosslinking agent and then with the aqueous solution of a polymeric material of biological origin in the step (d). Further, the water-soluble powder used in the step (b) may be replaced with a homogeneous mixture of the water-soluble powder and a synthetic resin short fiber.

As the elastomeric material constituting the artificial blood vessel of this invention, those polymers which have excellent compatibility with blood or tissue and do not induce inflammation of the tissue around the implanted vessel over an extended period after implantation are preferably used. Such polymers can be exemplified by polyvinyl halides, polystyrenes and derivatives thereof, polyolefins, polyesters, celluloses, polyurethanes, polysulfones and polyamides. These polymers may assume a form of copolymer or mixture. Taking mechanical properties, stability in a living body, antithrombotic properties, etc. into consideration, polyurethane series polymers are preferred, which typically includes polyurethane, polyurethaneurea, mixtures of such polymers with silicon polymers, or such polymers forming an intertwined reticular structure with silicon polymers. The polyurethane series polymers may include segmented polyurethanes or polyurethaneureas, those containing polydimethylsiloxane in the principal chain and those containing fluorine in the hard or soft segment. The polyether type polyurethanes or polyurethaneureas are preferred to the polyester type ones in that the former are hardly susceptible to biodegradation.

As the solvent for forming a solution of an elastomeric material, good solvents therefor, particularly those which can be handled and removed easily, are preferred, and typically includes tetrahydrofuran, dioxane, acetone, dimethylformamide and dimethylacetamide. These solvents may be used in admixture with a poor solvent, as necessary.

While the concentration of an elastomeric material in the solution may not particularly be limited so long as the solution can form a solution layer, it is usually 5 to 35 wt %, preferably 5 to 25 wt %. If the concentration of the elastomeric material is too high, the speed that the elastomer solution intrudes into the cavities between the water-soluble powders serving as the pore-forming agent or of the homogeneous mixture of such powder with a reinforcing short fiber will be too slow unfavorably, although the resulting artificial blood vessel may have a higher strength; whereas if the concentration is too low, the resulting artificial blood vessel comes to have a low strength, although it may have a sufficient thickness.

As the reinforcing material for the layer (A), knitted or woven fabrics such as a knitting or mixed weave of polyester, polypropylene, polyethylene and fluororesins can be used. The monofilament of such fabric is of 100 D (deniers) or less; while the multifilament is of 10 to 1,000 D, preferably 20 to 800 D, more preferably 30 to 500 D consisting of at least one filament. If the multifilament is of greater than 1,000 D, or if the monofilament is of greater than 100 D, the thickness of the reinforcing material to be incorporated in the layer (A) will be too great and provides very poor suturing performance when anastomosed with a living blood vessel. Particularly when such artificial blood vessel is used for hemodialysis, it provides poor puncturing performance when hemodialysis is carried out. If the multifilament is of less than 10 D, the resulting reinforcing material becomes too thin to provide sufficient strength under the pulsation repeated for a long time. Particularly when such artificial blood vessel is used for hemodialysis, it is difficult for it to retain sufficient strength, since the portion of the vessel wall between one hole and another adjacent thereto formed by puncturing at the site where localized puncturing is repeated for a long time, is gradually stretched by the creep and finally ruptures. While the presence of the reinforcing material allows the artificial blood vessel to have a crimped shape and retain the shape, use of a multifilament of less than 10 D makes it difficult to let the artificial blood vessel have and keep the crimed shape. The knitted or woven fabric used here may be in the form of sheet or tube having a thickness of 0.01 to 2.0 mm. The knitted or woven fabric should be present at the site at least except for the both end portions (the end portions being 20% or less of the entire length) of the artificial blood vessel, particularly at the site where it is subjected to puncturing as the blood access.

As the synthetic resin short fiber to be used as the reinforcing material for the layer (B) or (C), polyester, polypropylene, polyethylene, nylon, Teflon, etc. can be used.

The layer (A) has independent closed cells having a diameter of 0.01 to 500 µm, preferably 0.01 to 100 µm, in which large closed cells having an average diameter of 10 µm or more are present. These closed cells characteristically have noncommunicability. If the diameter of such closed cell is less than 0.01 µm, the layer (A) is densified to assume a state where there is substantially no cells, so that the vessel wall becomes stiff to provide poor needling performance and antikinking properties. If the diameter of such closed cell is greater than 500 µm, pinholes may easily be formed and the cells cannot maintain noncommunicability over the thickness of the vessel wall. Moreover, after a long period of use, the creep induced by pulsation causes the pinholes to be enlarged or cracking around the holes, leading readily to forming seroma, hematoma or aneurysm. Particularly when the artificial blood vessel is used for hemodialysis, it has insufficient strength against localized puncturing for an extended period.

When the layer (A) is to be formed, for example in the case of the artificial blood vessel A, for example, a solution of an elastomeric material dissolved in a good solvent therefor such as dimethylacetamide or a mixed solvent of dimethylacetamide and tetrahydrofuran is applied on the circumference of a chromium-plated stainless steel mandrel having a diameter corresponding to the desired size of artificial blood vessel, and immersed in water to effect solidification speedily and also removal of the solvent therefrom, followed by drawing the solidified elastomeric material off from the mandrel, washing and drying (to form a pseudo-layer (A)). Subsequently, the solution of an elastomeric material is coated at least onto the inner surface of the pseudo-layer (A) (this operation allows the surface of the pseudo-layer (A) on which the solution of an elastomeric material is applied to be partly dissolved), and a water-soluble powder or a homogeneous mixture of the water-soluble powder and a synthetic resin short fiber is deposited on the coated surface. After leaving to stand for a predetermined time, the elastomeric material applied later is solidified and desolvated in water to form a new layer [layer (B)] (this operation also effects solidification and desolvation of the partly dissolved layer of the pseudo-layer (A) to form a layer (A) having its surface contiguous to the layer (B) being modified physically).

Meanwhile, in the case of the artificial blood vessel B, for example, a polyester knitting tube is fitted as a reinforcing material on the mandrel and impregnated with a relatively dilute solution of an elastomeric material dissolved in a good solvent therefor such as tetrahydrofuran, followed by drying (to form a porous elastomer having a knitted or woven fabric incorporated in the layer, which is hereinafter referred to as primary layer (A)). Then, the mandrel is then immersed in a solution of an elastomeric material dissolved in a good solvent, for example dimethylacetamide or a mixed solvent of dimethylacetamide and tetrahydrofuran, drawn up from the solution, and then immersed in water to effect solidification speedily and also to remove the solvent therefrom, followed by drying. By repeating the above procedures until a predetermined thickness is obtained, a layer containing a multiplicity of cells (hereinafter referred to as additional layer) can be formed on the outer surface of the primary layer (A). The formation of the additional layer may, as necessary, be carried out after the primary layer (A) is drawn off from the mandrel so as to form additional layers on the inner and outer surfaces of the primary layer (A) simultaneously. Alternatively, the same solution of an elastomeric material may be applied to the inner surface of the primary layer (A) after it is drawn off from the mandrel, and the excessive solution is removed. The tube is then immersed in water, followed by the same procedures as described above to form an additional layer on the inner surface of the primary layer (A) (the product obtained here corresponds to the pseudo-layer (A)). Subsequently, the solution of an elastomeric material is coated at least onto the inner surface of the pseudo-layer (A) (this operation allows the surface of the pseudo-layer (A) on which the solution of an elastomeric material is applied to be partly dissolved), and a water-soluble powder or a homogeneous mixture of the water-soluble powder and a synthetic resin short fiber is deposited on the coated surface. After being left to stand for a predetermined time, the elastomeric material applied later is solidified and desolvated in water to form a new layer [layer (B) ] (this operation also effects solidification and desolvation of the partly dissolved layer of the pseudo-layer (A) to form a layer (A) having its surface contiguous to the layer (B) being modified physically).

The thus formed layer (A) has a multiplicity of closed cells, so that it can give flexibility to the resulting artificial blood vessel and contribute to the prevention of kinking. Incidentally, the thickness of the layer (A) is 5 to 500 µm, particularly preferably 50 to 300 µm (in the case of an artificial blood vessel having a diameter of 5 to 6 mm).

Now, referring to the artificial blood vessel B, the reinforcing material incorporated in the primary layer (A) serves to exhibit shape retaining function. Accordingly, the primary layer (A) is then subjected to bellows-forming treatment, if necessary. The crimp-forming treatment can be carried out by fitting the pseudo-layer (A) obtained above on a mandrel, and winding spirally a thread made of an appropriate material such as polyester, Teflon, polypropylene, etc. at a pitch of 0.5 to 10.0 mm, preferably 1.0 to 8.0 mm, more preferably 1.5 to 6.0 mm (if the pitch is greater than 10.0 mm, the artificial blood vessel cannot maintain antikinking properties and is liable to be collapsed during the operation or after operation in a linving body; whereas if the pitch is smaller than 0.5 mm, the resulting artificial blood vessel can show poor suturing performance and particularly poor puncturing performance in dialysis when the artificial blood vessel is used for hemodialysis). The thus treated tube is then immersed in a solvent, such as an alcohol, which can swell the pseudo-layer (A) but cannot dissolve the pseudo-layer (A) and the thread. Subsequently, the tube is drawn off once from the solvent, compressed longitudinally under aerobic conditions to give a crimped shape and reimmersed in the solvent as such (for at least 12 hours so as to achieve sufficient swelling). The thus treated tube is then immersed in a solvent having compatibility with the above solvent but cannot dissolve the pseudo-layer (A) and the thread, preferably in water, to remove the former solvent, and the thread is removed, followed by adjustment of the pitch of the bellows to conform with the pitch of the thread wound spirally around the tube.

The process of forming open cells in the layer (B) in order to allow the layer (B) to exhibit the intended function thereof is applied at least to the inner surface of the layer (A), since the main role of the layer (B) is to provide good binding with the intimal tissue. This process can be carried out according to the technique as disclosed in Japanese Provisional Patent Publication (KOKAI) No. 64-65143/1989. More specifically, the solution of an elastomeric material dissolved in the solvent is coated thinly onto the inner surface or the inner and outer surfaces of the pseudo-layer (A), and a water-soluble powder having an average particle size of 5 to 150 µm, for example, a salt such as sodium chloride, sodium sulfate, sodium carbonate and sodium acetate, a water-soluble starch and a casein, preferably a water-soluble starch or a homogeneous mixture of the water-soluble starch and a synthetic resin short fiber (length: ca. 0.5 mm) such as a polyester short fiber is deposited on the coated layer by spraying using a carrier gas such as $N_2$ to form a layer having a uniform thickness, followed by leaving to stand for a while. During this while, the elastomer solution coated onto the surface of the layer (A) intrudes into the cavities between the powder or of the mixture of the powder and the fiber (powder/short fiber mixture) by the capillary action, and the layer of the elastomer solution assumes a state as if it contains the powder or the powder/short fiber mixture dispersed homogeneously throughout the layer. Accordingly, the amount of the powder or of the powder and the short fiber to be deposited (thickness of the layer of the powder or the powder/fiber mixture) is correlated with the amount of the elastomer solution to be intruded into the cavities. While the standing time after the powder or the powder/short fiber mixture is deposited may depend on the factors such as the viscosity of the elastomer solution, wettability of the powder or the powder/short fiber mixture and packing condition of the powder or the powder/short fiber mixture, it is usually several seconds to several minutes.

Next, the thus treated tube is immersed in water to effect solidification of the elastomeric material applied, and then in hot water to dissolve and remove the powder therefrom, followed by drying, to form a layer (B) containing open cells with a diameter of 5 to 150 µm which are connected to one another with the pores having a diameter of 3 µm or more (when the elastomer solution is applied only on the inner surface of the pseudo-layer (A)), or similar layers (B) and (C) (when the elastomer solution is applied on the inner and outer surfaces of the pseudo-layer (A)).

In the case of the artificial blood vessel B having been subjected to crimp-forming treatment, the step of forming a uniform layer (B)or layers (B) and (C)may be carried out while the crimp formed in the preceding step is stretched longitudinally (with the pitch of the crimp being stretched). In this case, the pitch of the bellows is adjusted to conform with the pitch of the thread having been wound spirally thereon, after the layer (B) or the layers (B) and (C) are formed.

In order to form a crosslinked coat, the tube having the layer (B)or layers (B) and (C) formed contiguous to the layer (A) is immersed in an aqueous solution of a polymeric material of biological origin having a concentration of 0.01 to 20 wt %., preferably 0.1 to 10 wt %, more preferably 0.5 to 5 wt % such as gelatin, collagen, atherocollagen and albumin, under reduced pressure to impregnate the tube with the aqueous solution, and after the tube is drawn off therefrom, it is cooled speedily to 5° C. or lower to effect gelation of the impregnated aqueous solution, followed by immersion in an aqueous solution of a crosslinking agent (>1 wt %) such as glutaraldehyde at room temperature for at least one minute to effect crosslinking. The reason why immersion in the aqueous solution of polymeric material of biological origin is carried out under reduced pressure is to evacuate the air present in the open-cell structure and allow the aqueous solution to intrude deeply into the structure. Thus, the wall surface of open-cell structure can deeply be coated with the crosslinked polymer of biological origin, so that the intimal tissue can intrude deep into the open-cell structure and firmly immobilized onto the artificial blood vessel. The reason why the tube is cooled after impregnation with the aqueous solution of polymeric material of biological origin is to effect gelation of the aqueous solution and prevent the limp hanging of the aqueous solution intruded into the open-cell structure and form a coat having a uniform thickness without clogging the open cells. Thus, the gelled aqueous solution intruded into the cells is made hardly soluble in the aqueous solution of crosslinking agent when contacted therewith in the subsequent crosslinking operation, whereby the desired degree of crosslinking can be achieved with no diffusion of the gelled layer.

The crosslinking may also be carried out as follows: The tube is immersed in the aqueous solution of a crosslinking agent having a concentration as specified above, and after it is immersed in a current water to remove the excessive solution therefrom, it is immersed in the aqueous solution of a polymeric material of biological origin preliminarily adjusted to the concentration as specified above.

The tube subjected to crosslinking using any of the above methods is finally immersed in an alcohol to remove fully the excessive aqueous solution of crosslinking agent, followed by drying. This final treatment allows the tube to be coated with a crosslinked polymer on the inner surface or on the inner and outer surfaces maintaining mutual communicability of the open cells formed preliminarily on the surface or surfaces thereof with no clogging of the open cells. It should be noted here that while the concentration of the aqueous solution of polymeric material of biological origin may suitably be selected from the range specified above depending on the desired thickness of the coat, it will be difficult to form a uniform thickness of the coat if it exceeds 20 wt %; and if the thickness of the coat is too great, the open cells or the pores connecting the open cells will be clogged to impair mutual communicability, unfavorably. On the other hand, if the concentration is less than 0.01 wt %, the coat may come to have flaws.

In the case of the artificial blood vessel B having been subjected to crimp-forming treatment, the step of forming a uniform thickness of the coat may be carried out while the bellows formed in the preceding step is stretched longitudinally (with the pitch of the crimp being stretched). In this case, the pitch of the crimp is adjusted to conform with the pitch of the thread having been wound spirally thereon, after the coat is formed.

The thus obtained artificial blood vessel (A or B) can further be subjected to a bending treatment so as to conform the form of the artificial blood vessel to the site to which it is implanted. For example, the artificial blood vessel is fitted on a desired form of metal rod and then immersed in a solvent in which the artificial blood vessel can be swollen but not dissolved, such as an alcohol, (for at least 12 hours so as to effect swelling sufficiently). Subsequently, the artificial blood vessel is immersed in a solvent which has compatibility with the former solvent but cannot dissolve the artificial blood vessel therein, preferably in water, to remove the former solvent, followed by drying. The thus treated artificial blood vessel can readily be implanted to the intended site without application of any further bending operation and can retain its shape for a long time with no fear of collapsing after implantation into a living body. Even the artificial blood vessel A which is not subjected to bellows-forming treatment is also free from the fear of kinking in a living body if the bending treatment is applied thereto.

Since the layer (A) of the present artificial blood vessel has a closed-cell structure, it has a porosity (amount of leaked water/$cm^2$·min·120 mmHg) of substantially zero. The percentage of void of the entire vessel wall is 10 to 80%, preferably 20 to 60%. If the percentage of void is greater than 80% it is likely that the pores are expanded or cracked by the creep induced by pulsation repeated for a long time; whereas if it is smaller than 10%, the artificial blood vessel comes to have poor suturing performance, particularly poor puncturing performance.

The present artificial blood vessels has a compliance to be calculated from the following equation of 0.3 or less, preferably 0.1 or less. If the compliance is greater than 0.3, the artificial blood vessels is readily susceptible to the influence of creep induced by pulsation repeated for a long time, unfavorably.

$$\text{Compliance} = (V_{150} - V_{50})/V_{50}$$

$V_{150}$: luminal volume of the artificial blood vessel when an inner pressure of 150 mmHg is applied $V_{50}$: luminal volume of the artificial blood vessel when an inner pressure of 50 mmHg is applied

The following reference letters and numbers are used in the drawings:

| A | layer (A) | B | layer (B) | C | layer (C) |
|---|---|---|---|---|---|
| 1 | short fiber | 2 | closed cell | 3 | open cell |
| 4 | coat of crosslinked polymer | | | | |
| 5 | knitted fabric | | | | |

BEST MODE FOR CARRYING OUT THE INVENTION

Examples of producing the artificial blood vessels according to this invention will be described below.

EXAMPLE 1

(1) A polytetramethyleneglycol terminated at both ends with hydroxyl groups and having a molecular weight of 1,500 was reacted with 4,4'-diphenylmethaneisocyanate to obtain a prepolymer terminated at both ends with isocyanate groups. Subsequently, the prepolymer was reacted with butanediol to obtain a polyurethane (average molecular weight: $1.2 \times 10^4$). The thus obtained polyurethane was purified by repeating reprecipitation three times in total in a mixed solvent of tetrahydrofuran-ethanol system. The purified polyurethane was dissolved in a mixed solvent of dimethylacetamide (60%) and tetrahydrofuran (40%) to prepare a solution having a polyurethane concentration of 17 wt %.

(2) Into the polyurethane solution prepared in the step (1), extruded in a constant rate through an orifice having an inner diameter of 7 mm was a chromium-plated stainless steel mandrel having an outer diameter of 5.5 mm and a surface roughness of 0.3 μm, set to be coaxial with the orifice, so as to apply the polyurethane solution over the entire circumference of the mandrel to a uniform thickness. The thus treated mandrel was immediately introduced in a 25° C. water to effect solidification of the polyurethane applied thereon speedily from the outer surface, and retained therein for a while to remove the solvent therefrom. After the mandrel was drawn up from the water, the solidified polyurethane was drawn off from the mandrel, washed and dried in an air oven heated to about 30° C. (for 6 hours) to obtain a tube-I having an inner diameter of 5.3 mm and an outer diameter of 6.8 mm.

(3) After the polyurethane solution was coated onto the inner and outer surfaces of the tube-I, the excessive solution was removed, and a mixture of a water-soluble starch (particle size: 20 to 100 μm) and a polyester short fiber having a length of about 0.5 mm was deposited thereon by spraying using a carrier gas, followed by leaving to stand for one minute. The thus treated tube-I was immersed in water to effect solidification of the polyurethane coated thereon and also desolvation. Subsequently, the thus treated tube-I was immersed in a 60° C. water for 3 hours to dissolve and remove the starch, washed with water and then dried in an air oven heated to about 30° C. to obtain a tube-II consisting of new layers [layers (B) and (C)] both containing open cells formed on the inner and outer surfaces of the tube-I, and a layer [layer (A)], containing closed cells, present contiguous to the layers (B) and (C).

(4) The tube-II was immersed in a 1 wt % aqueous gelatin solution under reduced pressure so as to impregnate the tube with the aqueous solution, and cooled speedily to 5° C. to effect gelation of the impregnated gelatin. Subsequently, the thus treated tube-II was immersed in a 15 wt % aqueous glutaraldehyde solution for 10 minutes to effect crosslinking of the gelatin. The thus treated tube-II was immersed in an alcohol to remove fully the excessive glutaraldehyde therefrom and then in water to remove the alcohol by replacement with water. The tube-II was finally dried in a 30° C. air oven for 3 hours to obtain an artificial blood vessel (inner diameter: 5.0 mm, outer diameter: 6.5 mm) with the surfaces of the layers (B) and (C) and the wall surfaces of open cells being coated with a thin film of crosslinked gelatin. Subsequently, the artificial blood vessel was fitted on a U-shaped metal rod and immersed in an alcohol (for 24 hours), and after the alcohol was replaced with water, it was dried (to obtain an artificial blood vessel bent).

Figure 1:
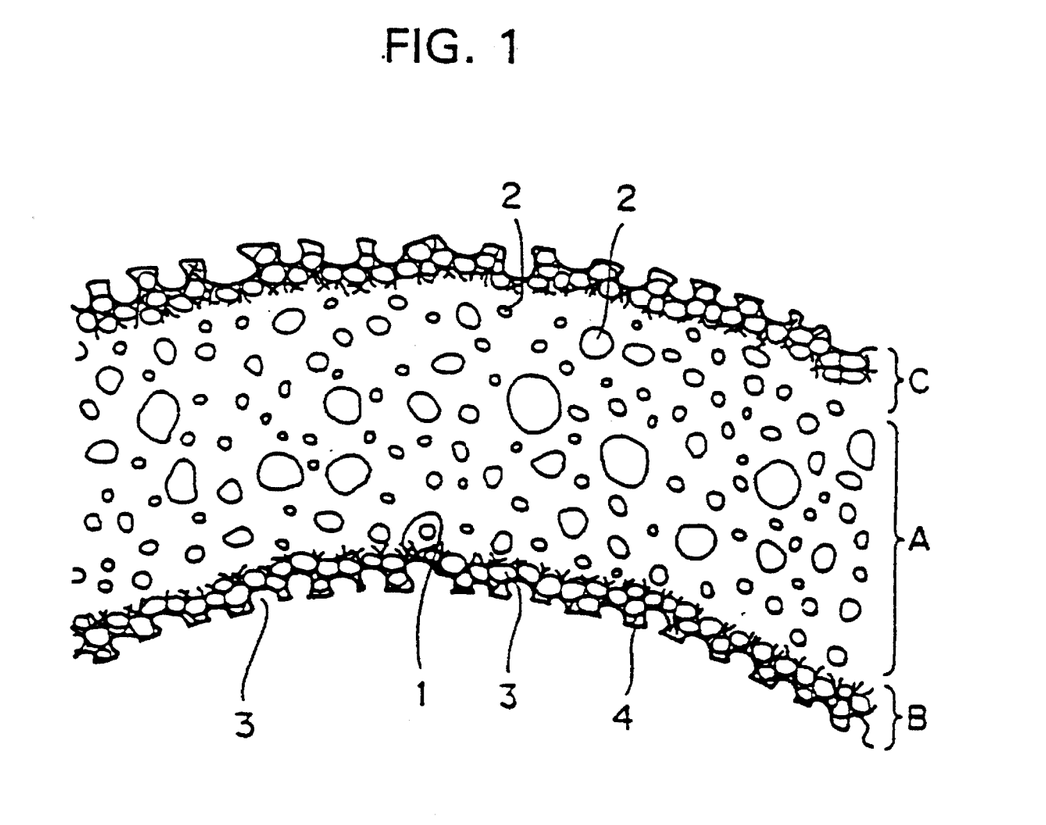
FIG. 1 shows schematically the cross section of the artificial blood vessel A produced according to Example 1 of this invention.

The cross section of the thus obtained artificial blood vessel (artificial blood vessel A) is schematically shown in FIG. 1.

The layers (B) and (C) of this artificial blood vessel both had a thickness of 150 μm, in which a polyester short fiber was distributed at random with minute cells (average diameter: 15 to 70 μm; a percentage of void: 96 to 98%) opening toward each surface of the vessel wall; wherein each cell was partitioned with a fibrous or thin-sheet-like polyurethane. Observation of the cross section of this artificial blood vessel identified that the cells are connected to one another with pores having a diameter of 3 μm or more and that the open cells formed in the step (3) and the pores connecting these cells are maintained as such even after coating with the crosslinked gelatin. It was also identified that the inner and outer layers have the same structure at any site, and that a layer (A) having a thickness of 300 μm containing a multiplicity of independent spherical closed cells having a diameter of about 10 to 100 μm is present between the layers (B) and (C) demarcated from them.

When the lumen of the artificial blood vessel was filled with a bovine blood and an internal pressure of 300 mmHg was applied thereto for 48 hours, there was observed no permeation of serum through the vessel wall. The artificial blood vessel used for the above test was washed with a physiological saline and fixed with glutaraldehyde. When the thus treated vessel was used as a specimen and subjected to observation of its cross section using a metallographical microscope, it was identified that no blood intruded into the closed cells present in the layer (A) and thus the vessel wall of the present artificial blood vessel has blood impermeability.

The thus obtained artificial blood vessel with a length of 10 cm was implanted subcutaneously as a bypass between a carotid artery and a juglar vein to an adult mongrel dog. After two weeks, a part of the anastomosed portion of the artificial blood vessel on the artery side was resected. When the state of the resected piece of the artificial blood vessel was observed, it was identified that the crosslinked gelatin coated onto the layers (B) and (C) was present without being decomposed. After three weeks, when an injection needle No. 18G was pierced into the artificial blood vessel from the outside, the needle smoothly penetrated through the vessel wall. When the needle was left to stand as such for 4 hours and then pulled out, bleeding completely stopped after about 10 seconds, and thus it was identified that the present artificial blood vessel has excellent hemostatic performance. When 5 times of puncturing a day was repeated for the same artificial blood vessel for 6 months thereafter, the present artificial blood vessel showed excellent performance as the blood access for hemodialysis free from hematoma or seroma. When the artificial blood vessel was resected after 10 months to observe the state thereof, it was found that the connective tissue formed on the outer surface was firmly bound to this artificial blood vessel, while the inner surface of the artificial blood vessel was free from pannus or thrombus. It was also identified that the intima particularly at the anastomosed portion of this artificial blood vessel intruded to the depth of about 120 μm from the surface of the layer (B) and firmly bound to the artificial blood vessel. It was further observed that no kinking occurred. Meanwhile, although there was observed a cracking in this artificial blood vessel formed by the puncture holes which were connected with one another at the site subjected to localized puncturing, the degree of cracking was not so heavy as to cause complicating disease, e.g. formation of hematoma.

EXAMPLE 2

An artificial blood vessel having an inner diameter of 3.5 mm and an outer diameter of 5 mm was produced in the same manner as in Example 1, except that a stainless steel mandrel used in the step (2) of Example 1 was replaced with one having a smaller diameter and that no bending treatment was applied. The thus obtained artificial blood vessel with a length of 10 cm was implanted to an iliac artery of an adult mongrel dog. The artificial blood vessel was sutured easily with no bleeding through the needle holes. The implanted piece of artificial blood vessel showed good patency even after 16 months. After 18 months, the implanted piece of artificial blood vessel was resected to observe the state thereof, and it was identified that the surface of the layer (C) was covered with a connective tissue having a thickness of about 0.2 mm. The adhesion of the connective tissue was so firmly achieved that it cannot be peeled completely therefrom. It was identified that the inner surface at the anastomosed portion was connected smoothly with the living blood vessel and that a thin intima having a thickness of 0.1 to 2 mm was covering the entire surface of the layer (B) and the intimal tissue was also intruding into the depth of about 150 μm from the surface of the layer (B) to be firmly bonded to the artificial blood vessel. The artificial blood vessel produced according to the present process showed very excellent performance as a small-diameter artificial blood vessel to be implanted at such site where it is not subjected to frequent puncturing.

EXAMPLE 3

(1) To a chromium-plated stainless steel mandrel having an outer diameter of 5.5 mm was fitted a polyester knitting tube (consisting of a 50 D multifilament) having a thickness of 0.2 mm and an inner diameter which is substantially the same as the outer diameter of the mandrel, and the mandrel was immersed (20 seconds) at room temperature in a solution of the purified polyurethane obtained in the step (1) of Example 1 dissolved in tetrahydrofuran to impregnate the fibers constituting the tube with the solution so as to fill the vacancies present therein and also to coat the inner circumference of the tube to form a uniform thickness of solution layer. The thus treated tube was dried (3 hours) in a 20° C. air oven to provide a tube-III (primary layer (A)).

(2) The mandrel with the tube-III fitted thereon is immersed (20 seconds) in a solution of the purified polyurethane dissolved in dimethylacetamide (polyurethane concentration: 20 wt %) so as to deposit the polyurethane solution on the circumference of the primary layer (A) to form a uniform thickness of solution layer (i.e. additional layer). The resulting tube was immediately introduced into a 35° C. water to effect solidification of the polyurethane deposited thereon speedily from the outer surface and retained therein for a while to remove the solvent. Subsequently, the mandrel was drawn up from the water and dried in a 35° C. air oven for 3 hours. The above operation was repeated until a desired thickness of additional layer is formed, and the tube was finally drawn off from the mandrel to obtain a tube IV (pseudo-layer (A)) (inner diameter: 5.3 mm, outer diameter: 6.8 mm) consisting of the tube-III with an additional layer formed on the outer surface thereof.

(3) After the tube-IV was fitted again on the mandrel, a Teflon thread was wound spirally on the circumference of the tube-IV and immersed (3 hours) in an alcohol. The mandrel was drawn up once from the alcohol and the tube-IV was compressed longitudinally to give a crimped shape (the resulting tube is referred to as tube-V). Subsequently, the tube-V was immersed again in the alcohol to effect swelling thereof sufficiently and then immersed in water to remove the alcohol by replacement with water. The thread wound thereon was removed and then the tube-V was stretched longitudinally so that the pitch of the bellows may conform with that of the thread wound thereon, followed by drying in a 35° C. air oven for 3 hours. The mandrel was finally pull away from the thus treated tube having a predetermined pitch of crimp (tube-VI or pseudo-layer (A) having a crimped shape).

(4) The tube-VI was coated with the polyurethane solution used in the step (2) on the inner and outer surfaces thereof with the crimp stretched longitudinally (with the pitch of the crimp stretched), wherein the substantial amount of the polyurethane solution applied here finally constitutes the layers (B) and (C) (this operation partly dissolves the surface of the pseudo-layer (A)). A water-soluble starch powder (particle size: 5 to 150 μm) was deposited on the coated surface by spraying using a carrier gas, followed by leaving to stand for one minute. The resulting tube was immersed in water to effect solidification of the polyurethane (wherein the partly dissolved surface of the pseudo-layer (A) can also be solidified by this operation to finally convert the pseudo-layer (A) into layer (A)), followed by immersion in a 60° C. water for 5 hours to dissolve and remove the starch powder and then drying in a 35° C. air oven for 3 hours to form layers (B) and (C), containing open cells throughout the layers, contiguous to the inner and outer surfaces of the layer (A), respectively (the resulting tube is referred to as tube-VII).

(5) The tube-VII was immersed under reduced pressure in a 1 wt % aqueous gelatine solution with the crimp thereof being stretched longitudinally (with the pitch of the crimp being stretched). After the tube was impregnated with the aqueous solution, it was cooled speedily to 5° C. to effect gelation of the impregnated gelatin, followed by immersion in a 15 wt % aqueous glutaraldehyde solution for 10 minutes to effect crosslinking of the gelatin. The thus treated tube was immersed in an alcohol to remove completely the excessive glutaraldehyde and then in water to remove the alcohol by replacement with water, followed finally by drying in a 35° C. air oven for 3 hours, pitch adjustment of the crimp so as to conform with the pitch as achieved in the step (3) to give an artificial blood vessel (inner diameter: 5.0 mm, outer diameter: 6.5 mm) with the surfaces of the layers (B) and (C) and the wall surfaces of open cells being coated with a thin film of crosslinked gelatin.

Figure 2:
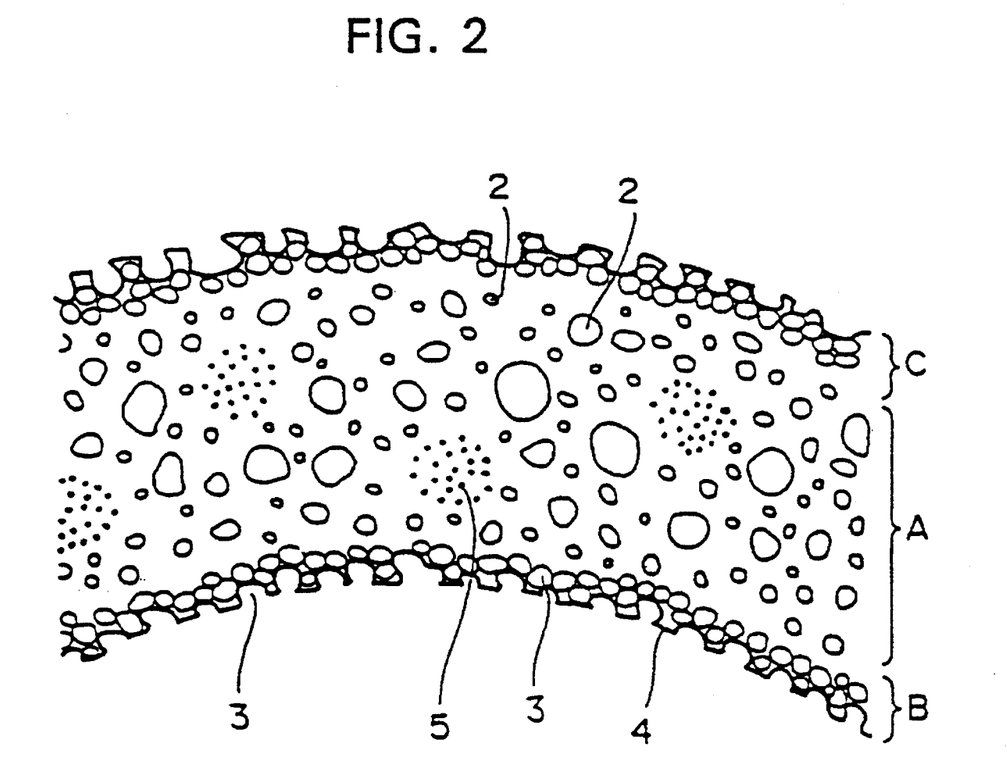
FIG. 2 shows schematically the cross section of the artificial blood vessel B produced according to Example 3 of this invention.

The cross section of the thus obtained artificial blood vessel (artificial blood vessel B) is schematically shown in FIG. 2.

The thus obtained artificial blood vessel with a length of 10 cm was implanted subcutaneously as a bypass between a carotid artery and a juglar vein to an adult mongrel dog. After two weeks, when an injection needle No. 18G was pierced into the artificial blood vessel from the outside, the needle smoothly penetrated through the vessel wall. When the needle was left to stand as such for 4 hours and then pulled out, bleeding completely stopped after 10 seconds, showing excellent hemostatic performance. When 5 times of puncturing a day was repeated for the same artificial blood vessel for 6 months thereafter, the present artificial blood vessel showed excellent performance as the blood access for hemodialysis free from hematoma or seroma. When the artificial blood vessel was resected after 10 months to observe the state thereof, it was found that the connective tissue formed on the outer surface was firmly bound to this artificial blood vessel. The inner surface of the artificial blood vessel was smoothly connected with the living blood vessel with no notable formation of pannus. Further, neither kinking nor formation of pseudoaneurysm was observed in the present artificial blood vessel.

COMPARATIVE EXAMPLE

An artificial blood vessel was produced in the same manner as in Example 3, except that the reinforcing material was not incorporated to the layer corresponding to the layer (A), that neither the crimp-forming treatment nor the bending treatment was carried out, and that the layers corresponding to the layers (B) and (C) and the wall surfaces of open cells were not coated with the crosslinked gelatin.

The thus obtained straight artificial blood vessel with a length of 10 cm was implanted subcutaneously to form a U-shape as a bypass between a carotid artery and a juglar vein to an adult mongrel dog. After three weeks, when 5 times of puncturing a day was repeated for the same artificial blood vessel for 6 months, the present artificial blood vessel was free from hematoma or seroma. However, when the artificial blood vessel was examined by angiography, vasoconstriction was observed at the anastomosed portion, and the artificial blood vessel was obturated after two more months. When the artificial blood vessel was resected to observe the state thereof, it was found that the connective tissue formed on the outer surface was surrounding this artificial blood vessel with no peeled portion. However, when the connective tissue was pulled with fingers, it partly came off.

There was further observed hyperplasia on the inner surface around the anastomosed portion of the artificial blood vessel with the peripheral portion of the tissue coming off and obturation of the artificial blood vessel with thrombi. Further, no intrusion or growth of the intimal tissue into the internal portion of the layer corresponding to the layer (B) was observed.

Meanwhile, there was found some cracked portions formed by the connection of puncture holes at the site which was subjected to localized puncturing, and further the implanted artificial blood vessel to form a U-shape had a flat cross section at the longitudinal middle portion. However, the artificial blood vessel was not collapsed so completely at said portion as to obturate the lumen thereof.

INDUSTRIAL APPLICABILITY

The artificial blood vessel according to this invention has the following characteristics.

(1) Since the entire vessel wall is of a structure containing a multiplicity of cells, it provides small contact area at the cut end face with a living blood vessel, so that healing of the living blood vessel can be accelerated with reduced stimulus generated by the repelling reaction to foreign body. Moreover, the artificial blood vessel shows improved needling performance with a suturing needle.

(2) At least the layer which is brought into direct contact with blood [layer (B)] is of a structure containing a multiplicity of open cells throughout the layer, and the surface of the layer (B) and the wall surfaces of open cells are coated with a thin film of crosslinked polymer of biological origin, so that the present artificial blood vessel can show improved adhesion with a living tissue to form firm bond therebetween. Further, granulation from the cut end faces of the living blood vessel or hyperplasia on the inner surface of the artificial blood vessel can be prevented, so that the present artificial blood vessel can stay stably in a living body with improved patency over an extended period.

(3) Since the layer (A) is of a structure containing a multiplicity of closed cells with no communicability across the thickness of the vessel wall, there is no leakage of plasma or blood through the vessel wall, leading to reduced bleeding after puncturing. Further, the present artificial blood vessel has flexibile vessel wall and thus can show improved needling performance with a suturing needle.

(4) The synthetic resin short fiber distributed at least throughout the layer (B) effectively improves the strength of the present artificial vessel, particularly the strength of the open cell structure of the layer (B) participating in the bond with the intimal tissue.

(5) Since particularly the artificial blood vessel B has a reinforcing material incorporated in the layer (A), it can exhibit excellent shape-retaining properties and durability under pulsation and repeated puncturing and also great mechanical strength. Accordingly, if the artificial blood vessel is used at a hemodialytic site for a long period, not only appearance of side effects such as formation of seroma, hematoma or aneurysm can be prevented but also the artificial blood vessel can readily be allowed to have a crimped shape and retain its shape.

(6) The present artificial blood vessel having been subjected to crimp-forming or bending treatment shows excellent antikinking properties.

What is claimed is:

1. An artificial blood vessel having a structure made of an elastomer containing a multiplicity of cells throughout the structure and comprising:

a first layer containing closed cells having no communicability therebetween, said first layer having an inner surface and an outer surface; and a second layer containing open cells having mutual communicability therebetween, said open cells of said second layer having wall surfaces;

said second layer having a first surface and a second surface, said first surface being contiguous to the inner surface of said first layer, the second surface of said second layer and said wall surfaces of said open cells of said second layer are coated with a thin film of a crosslinked protein of biological origin, without clogging said open cells; said crosslinked protein allowing intimal tissue to deeply intrude into said open cell structure of said blood vessel.

2. The artificial blood vessel according to claim 1 which additionally has, contiguous to the outer surface of said first layer, a third layer having a surface and containing open cells having mutual communicability therebetween, said open cells of said third layer having wall surfaces.

3. The artificial blood vessel according to claim 2, wherein said surface of said third layer and the wall surfaces of said open cells of said third layer are coated with a thin film of a crosslinked protein of biological origin.

4. The artificial blood vessel according to any of claims 1 to 3, wherein said first layer is incorporated with a reinforcing material selected from the group consisting of a knitted fabric and a woven fabric, said fabric being resistant to degradation when in a living body.

5. The artificial blood vessel according to claim 4, wherein the reinforcing material is selected from the group consisting of polyester, polypropylene, polyethylene and fluororesin.

6. The artificial blood vessel according to any of claims 1 to 3, wherein said second layer and/or said third-layer contains a synthetic resin short fiber distributed throughout said second layer and/or said third layer.

7. The artificial blood vessel according to claim 6, wherein the synthetic resin short fiber is selected from the group consisting of polyester, polypropylene, polyethylene, nylon and Teflon.

8. The artificial blood vessel according to claim 5, wherein at least the second surface of the second layer is corrugated.

9. The artificial blood vessel according to claim 4, wherein said second layer and/or said third layer contains a synthetic resin short fiber distributed throughout said second layer and/or said third layer.

10. The artificial blood vessel according to claim 5, wherein said second layer and/or said third layer contains a synthetic resin short fiber distributed throughout said second layer and/or said third layer.

11. (Amended) The artificial blood vessel according to claim 8, wherein said second layer and/or said third layer contains a synthetic resin short fiber distributed throughout said second layer and/or said third layer.

12. The artificial blood vessel according to claim 9, wherein the synthetic resin short fiber is selected from the group consisting of polyester, polypropylene, polyethylene, nylon and Teflon.

13. The artificial blood vessel according to claim 10, wherein the synthetic resin short fiber is selected from the group consisting of polyester, polypropylene, polyethylene, nylon and Teflon.

14. The artificial blood vessel according to claim 11, wherein the synthetic resin short fiber is selected from the group consisting of polyester, polypropylene, polyethylene, nylon and Teflon.

15. The artificial blood vessel according to claim 1, wherein said protein is selected from the group consisting of gelatin, collagen, atherocollagen and albumin.

16. The artificial blood vessel according to claim 3, wherein said protein is selected from the group consisting of gelatin, collagen, atherocollagen and albumin.

17. The artificial blood vessel according to claim 15, wherein the protein is crosslinked by glutaraldehyde; the elastomer is a polymer selected from the group consisting of polyvinyl halide, polystyrene, polyolefin, polyester, cellulose, polyurethane, polysulfone and polyamide; said first layer contains closed cells having a diameter of 0.01 to 500 $\mu m$; said first layer has a thickness of 5 to 500 $\mu m$; said second layer contains open cells with a diameter of 5 to 150 $\mu m$ and has pores with a diameter of 3 $\mu m$ or more; and the blood vessel has a vessel wall with a porosity of 20 to 60%.

18. The artificial blood vessel according to claim 17, wherein said first layer has a thickness of 50 to 300 $\mu m$; and the percentage of void of the vessel wall is 20 to 60%.

19. The artificial blood vessel according to claim 16, wherein said first layer is incorporated with a reinforcing material selected from the group consisting of polyester, polypropylene, polyethylene and fluororesin, said reinforcing material being selected from the group consisting of a knitted fabric and a woven fabric, and said fabric having a monofilament of 100 deniers or less, and having a multifilament of 10 to 1,000 deniers.

20. The artificial blood vessel according to claim 4, wherein at least the second surface of the second layer is corrugated.

21. The artificial blood vessel according to claim 1, wherein the artificial blood vessel has a compliance of 0.1 or less, wherein compliance is defined as $(V_{150}-V_{50})/V_{50}$, wherein $V_{150}$ is a luminal volume of the artificial blood vessel when an inner pressure of 150 mmHg is applied and $V_{50}$ is a luminal volume of the artificial blood vessel when an inner pressure of 50 mmHg is applied.

22. The artificial blood vessel according to claim 1, produced by a process comprising (a) uniformly applying a solution of an elastomeric material dissolved in a solvent on a circumference of a mandrel, followed by solidification and desolvation of the applied solution in water to provide a tube;

(b) coating said solution of the elastomeric material onto at least an inner surface of said tube, depositing a water-soluble powder on the resultant coated inner surface of said tube, allowing said tube to stand for a predetermined time, followed by solidification and desolvation of the elastomeric material in water to form a layer;

(c) removing the water-soluble powder deposited in step (b) by dissolving said tube in hot water to form open cells having mutual communicability therebetween in said layer formed in the step (b); and (d) impregnating said open cells formed in the step (c) with an aqueous solution of a polymeric material of biological original under reduced pressure, (e) rapidly cooling the impregnated tube from step (d) and (f) forming a thin film of crosslinked polymer on a surface of said layer and on the wall surfaces of said open cells formed in the step (c) by impregnation with an aqueous solution of a crosslinking agent, without clogging said open cells.

23. The artificial blood vessel according to claim 1, wherein the artificial blood vessel is disposed at a hemodialytic site.

24. An artificial blood vessel made of an elastomer containing a multiplicity of cells throughout, and being capable of having a crimped shape, comprising:

a first layer containing closed cells having no communicability therebetween, said first layer having an inner surface and an outer surface, said first layer being incorporated with a reinforcing material of a knitted or woven fabric which is resistant to degradation when in a living body; and a second layer containing open cells having mutual communicability therebetween, said open cells of said second layer having wall surfaces;

said second layer having a first surface and a second surface, said first surface being contiguous to said inner surface of said first layer and said second surface of said second layer and the wall surfaces of said open cells of said second layer are coated with a thin film of a crosslinked protein of biological origin, without clogging said open cells; said crosslinked protein allowing intimal tissue to deeply intrude into said open cell structure of said blood vessel.

25. The artificial blood vessel according to claim 24, which comprises a third layer containing open cells having mutual communicability therebetween and being contiguous to the outer surface of said first layer.

26. The artificial blood vessel according to claim 25, wherein said second layer and/or said third layer contains a synthetic resin short fiber distributed throughout said second layer and/or said third layer.

27. The artificial blood vessel according to claim 26, wherein the synthetic resin short fiber is selected from the group consisting of polyester, polypropylene, polyethylene, nylon and Teflon.

28. The artificial blood vessel according to claim 25, wherein said surface of the third layer and the wall surfaces of said open cells of said third layer are coated with a thin film of a crosslinked protein of biological origin.

29. The artificial blood vessel according to claim 24, claim 25 or claim 28, wherein the reinforcing material is selected from the group consisting of a polyester, polypropylene, polyethylene and a fluororesin.

* * * * *